United States Patent [19]

Coon

[11] 3,954,750

[45] May 4, 1976

[54] PREPARATION OF HEXAHYDRO-1,3,5-TRIALKANOYL-s-TRIAZINES

[75] Inventor: Clifford L. Coon, Fremont, Calif.

[73] Assignee: The United States of America as represented by the Secretary of the Army, Washington, D.C.

[22] Filed: Apr. 17, 1975

[21] Appl. No.: 569,032

[52] U.S. Cl. .......................................... 260/248 NS
[51] Int. Cl.$^2$ ...................................... C07D 251/04
[58] Field of Search .............................. 260/248 NS

[56] References Cited
OTHER PUBLICATIONS

Wegler et al., Chemische Berichte, Vol. 81, pp. 527–531, (1948).

*Primary Examiner*—John M. Ford
*Attorney, Agent, or Firm*—Nathan Edelberg; Robert P. Gibson; A. Victor Erkkila

[57] ABSTRACT

Hexahydro-1,3,5-trialkanoyl-s-triazines are produced by reacting a polymeric formaldehyde and an alkanoic acid amide in the presence of sulfuric acid catalyst and a liquid organic solvent or diluent while removing the water formed in the reaction by distillation, the amount of sulfuric acid catalyst employed being at least 0.05 mol per mol of said amide.

8 Claims, No Drawings

PREPARATION OF HEXAHYDRO-1,3,5-TRIALKANOYL-S-TRIAZINES

GOVERNMENTAL INTEREST

The invention described herein was made in the course of a contract with the Government.

BACKGROUND OF THE INVENTION

Hexahydro-1,3,5-triacyl-s-triazines are usually prepared by condensation of nitriles with formaldehyde in the presence of an acid catalyst under substantially anhydrous conditions. These compounds can also be prepared by employing the corresponding carboxamides in place of the nitriles and removing the water formed during the condensation, e.g., by azeotropic distillation with an organic liquid, such as toluene. However, as noted by R. Wegler and A. Ballauf, Chemische Berichte, 81, 527–31 (1948), who appear to be the only previous investigators of the reaction with carboxamides, the yields of hexahydro-1,3,5-triacyl-s-triazines obtained from the carboxamides never approach those obtained from the nitriles. Thus, they obtained hexahydro-1,3,5-tripropionyl-s-triazine in 26% of theory yield by heating a mixture of propionamide (1 mol), paraformaldehyde (1.2 mols), sulfuric acid (0.02 mol) and toluene to refluxing and removing the water formed in the reaction by azeotropic distillation.

The process of preparing hexahydro-1,3,5-trialkanoyl-s-triazines from alkanoic acid amides would provide substantial economic advantages over the conventional procedure using the corresponding nitriles if the yields of the triazines from such amides could be sufficiently increased.

SUMMARY AND DETAILED DESCRIPTION OF THE INVENTION

It is an object of the present invention to provide improvements in the process of producing hexahydro-1,3,5-trialkanoyl-s-triazines from carboxamides. It is a further object to provide a process for producing hexahydro-1,3,5-trialkanoyl-s-triazines in high yields from alkanoic acid amides.

It has been unexpectedly found that these and other objects can be obtained by reacting an alkanoic acid amide with a polymeric formaldehyde in the presence of a liquid organic diluent and a substantially larger proportion of sulfuric acid catalyst than employed in the prior art.

More particularly, the present invention is directed to a process for producing hexahydro-1,3,5-trialkanoyl-s-triazines of the general formula:

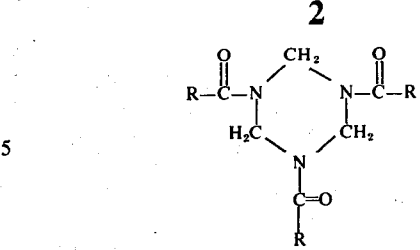

wherein R is an alkyl group of 1 to 20 carbon atoms, which comprises reacting an alkanoic acid amide of the formula $RCONH_2$, wherein R has the foregoing definition, and a polymeric formaldehyde in the presence of sulfuric acid catalyst and a liquid organic solvent or diluent while removing the water formed in the reaction by distillation, wherein the improvement comprises empolying at least 0.05 mol, and preferably about from 0.1 to 0.5 mol, of sulfuric acid per mol of said amide, particularly in conjunction with about 2 or more mols of formaldehyde equivalent per mol of said amide. The process of the present invention is preferably carried out at a temperature in the range about from 60°C. to 120°C.

The following examples illustrate specific embodiments of the process of the present invention.

Example 1 Preparation of Hexahydro-1,3,5-triacetyl-s-triazine (TRAT) From Acetamide and Paraformaldehyde.

To an agitated mixture of 59g (1 mol) acetamide, 60g (2 mols as $CH_2O$) paraformaldehyde and 3600 ml. toluene were added 14.0g (0.142 mol) conc. sulfuric acid. The resulting mixture was rapidly heated to boiling and refluxed for about 30 minutes while collecting water distilled as toluene/water azeotrope in a Dean-Stark trap. The hot solution was decanted from a small amount of a brown tarry substance and the toluene was removed by vacuum distillation, leaving a colorless semi-solid which solidified to soft white crystals on standing for several days. NMR analysis indicated that the product was almost pure TRAT. The product recrystallized from a mixture of hexane and chloroform yielded 63.8g of white crystals, corresponding to 90% of theory yield from acetamide.

In the following examples the foregoing procedure was repeated except that the amounts of sulfuric acid and paraformaldehyde were varied. The results are shown in Table 1.

Table 1

| Ex. No. | Acetamide g | mol | Paraformaldehyde g | mol* | g | Conc. $H_2SO_4$ mol mol/acetamide | Toluene ml | Reflux Time Hours | Yield of TRAT |
|---|---|---|---|---|---|---|---|---|---|
| 1 | 59 | 1 | 60 | 2 | 14.0 | 0.14 | 3600 | 0.5 | 90% |
| 2 | 59 | 1 | 60 | 2 | 7.0 | 0.07 | 3600 | 16 | 90% |
| 3 | 59 | 1 | 40 | 1.33 | 8.7 | 0.09 | 2600 | 0.8 | 80% |
| 4 | 59 | 1 | 40 | 1.33 | 17.4 | 0.18 | 2600 | 0.25 | 90% |

*as formaldehyde

Preparation of Hexahydro-1,3,5-tripropionyl-s-triazine (TRIP) From Propionamide and Paraformaldehyde

EXAMPLE 5

A mixture of 74g (1 mol) propionamide, 120g paraformaldehyde (90%) purity, 3.6 mols based on 100% purity, 3000 ml toluene and 20g (0.2 mol) conc. $H_2SO_4$ was heated to the boil and refluxed (temp. 110°C.) for about 15 minutes while collecting water distilled as water/toluene azeotrope in a Dean-Stark trap. The resulting solution was decanted from a small amount of a dark orange syrup and the toluene was removed by distillation under vacuo, leaving a white crystalline solid. Based on NMR spectrum of the product, TRIP was obtained in 90% of theory yield together with a small amount of methylene-bis-propionamide (MBP). The crude TRIP product was purified by recrystallization from 90% ethanol.

In Examples 6–8 tabulated below the procedure of Example 5 was repeated except that the proportions of paraformaldehyde and sulfuric acid catalyst as well as reflux times were varied.

Example 9

To a well stirred suspension of 74g (1 mol) of 97% propionamide and 120g (3.60 mols) of 90% paraformaldehyde in 3600 ml 1,2-dichloroethane were added 14g (0.142 mol) conc. $H_2SO_4$. The mixture was heated to reflux and refluxed for 18 hours, during which water formed was azeotropically distilled with the ethylene dichloride and collected in a Dean-Stark trap. The resulting solution was cooled to ambient temperature and decanted from a small amount of orange syrup. The solvent was removed by vacuum distillation, leaving 90.6g of a white crystalline solid, which by NMR analysis was shown to be almost pure TRIP containing a trace of methylene-bis-propionamide (MBP). Recrystallization of the product from 90% ethanol yielded 78g of pure TRIP, m.p. 165°–8°C., corresponding to a 93% yield.

Example 10

The procedure of Example 9 was repeated except that the reflux time was only 5 hours. A 90% yield of TRIP was obtained.

Example 11

To a well stirred mixture of 74g (1 mol) of 97% propionamide and 120g (3.60 mols) of 90% paraformaldehyde in 3000 ml of chloroform were added 14g (0.142 mol) conc. $H_2SO_4$. The mixture was heated to refluxing and refluxed for 4 hours while collecting water removed by azeotropic distillation in a Dean-Stark trap. The reaction mixture was cooled to room temperature and filtered to remove a small amount (1.1g) of a white solid. The solvent was removed from the filtrate by vacuum distillation, leaving 89.8g of a white, crystalline material. An NMR spectrum of this material showed that it consisted of a mixture of approximately 80% TRIP, 10% MBP and 10% 5-propionyldihydro-1,3,5-dioxazine.

Example 12

1.45g (0.143 mol) conc. $H_2SO_4$ were added to an agitated mixture of 74g (1.0 mol) of 97% propionamide and 120g (3.60 mols) of 90% paraformaldehyde in 3000 ml of methylene dichloride. The mixture thus obtained was refluxed for 20 hours while collecting water azeotropically distilled in a Dean-Stark trap. The reaction mixture was cooled to room temperature and filtered to remove a ball of an unidentified white solid (21.1g), which was insoluble in common organic solvents. The solvent was removed from the filtrate by vacuum distillation, leaving 61.2g of a white crystalline solid. An NMR spectrum of this product indicated that it contained approximately 50% TRIP along with other products including MBP and 5-propionyldihydro-1,3,5-dioxazine.

Table 2 sets forth a comparison of the experimental conditions and results of Examples 5–12 and shows that greatly increased yields of TRIP can be achieved by use of higher ratios of sulfuric acid catalyst than employed in the prior art.

The ratio of sulfuric acid employed as catalyst in the process of the present invention is at least 0.05 mol per mol of alkanoic acid amide. However, it is advanta-

TABLE 2

| Example | Chemische Berichte 81,531 (1948) | 5 | 6 | 7 | | 8 | 9 | 10 | 11 |
|---|---|---|---|---|---|---|---|---|---|
| Propionamide (mols) | 1 | 1 | 1 | 1 | | 1 | 1 | 1 | 1 |
| Paraformaldehyde (mols as formaldehyde) | 1.2 | 3.6 | 3.6 | 1.8 | | 1.2 | 3.6 | 3.6 | 3.6 |
| $H_2SO_4$ (mols per mol of propionamide) | 0.02 | 0.2 | 0.14 | 0.09 | | 0.09 | 0.14 | 0.14 | 0.14 |
| Organic solvent | not disclosed | toluene | toluene | toluene | | toluene | $ClC_2H_4Cl$ | $ClC_2H_4Cl$ | $CHCl_3$ |
| Reflux temperature | not disclosed | 110°C | 110°C. | 110°C. | | 110°C. | 83°C. | 83°C. | 60°C. |
| Reflux time (hours) | not disclosed | 0.25 | 0.25 | 0.5 | 3 | 18 | 0.25 | 18 | 18 | 5 | 4 |
| Yield TRIP (% theory) | 26 | 90 | 80 | 80 | 40 | 70 | 75 | 30 | 50 | 93 | 90 | 80 | geous to employ a larger ratio, preferably about from 0.1 to 0.5 mol of $H_2SO_4$ per mol of said amide, since such larger proportions usually produce the desired triazine compound in a shorter reaction time and/or higher yield. It has been found in many cases that as the amount of $H_2SO_4$ catalyst is increased substantially beyond about 0.2 mol per mol of amide, undesired reactions are promoted and the yield of hexahydro-1,3,5-trialkanoyl-s-triazine decreases roughly in molar proportion to such increased amounts of $H_2SO_4$. Accordingly, the use of subtantially larger ratios of $H_2SO_4$ than 0.5 mol/mol amide is generally undesirable.

Although equimolecular proportions of formaldehyde and alkanoic acid amide are theoretically required to form the hexahydro-1,3,5-trialkanoyl-s-triazine, it is usually advantageous to employ a higher ratio of formaldehyde to amide in the present process. Preferably, an amount of polymeric formaldehyde, e.g. paraformaldehyde and trioxane, equivalent to from about 2 to about 5 mols of formaldehyde per mol of the amide, is used. Substantially larger ratios of formaldehyde, e.g. up to about 10 mols or more per mol of amide can be utilized, but provide no further advantage and hence are relatively uneconomical.

The liquid organic solvent or diluent employed in the present process is inert to the reactants and is present in amount sufficient to provide a readily stirrable reaction mixture. Suitable organic liquids include hydrocarbons, such as n-hexane, benzene, toluene and xylene, and chlorinated hydrocarbons, such as methylene dichloride, 1,2-dichloroethane, 1,1,2-trichloroethane, chloroform and chlorobenzene. Toluene, 1,2-dichloroethane and chloroform are preferred organic liquids in view of their availability, economy and efficiency in the process of the present invention. Advantageously the organic liquid is distilled from the reaction mixture as an azeotrope with the water formed during the reaction.

Besides acetamide and propionamide illustraed in the foregoing examples, other alkanoic acid amides of the aforementioned general formula can be employed with similar results in the process of the present invention to produce the corresponding hexahydro-1,3,5-trialkanoyl-s-triazine compounds, including isobutyramide (R = (CH$_3$)$_2$CH—), hexanamide (R = CH$_3$(CH$_2$)$_4$—), lauramide (R = CH$_3$(CH$_2$)$_{10}$—) and stearamide (CH$_3$(CH$_2$)$_{16}$—).

The foregoing disclosure is merely illustrative of the principles of this invention and is not to be interpreted in a limiting sense. I wish it to be understood that I do not desire to be limited to exact details of construction shown and described for obvious modifications will occur to a person skilled in the art.

What is claimed is:

1. A process for preparing a hexahydro-1,3,5-trialkanoyl-s-triazine of the formula

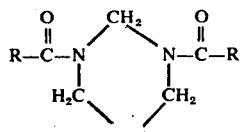

-continued

wherein R is an alkyl group of 1 to 20 carbon atoms, which comprises reacting an alkanoic acid amide of the formula RCONH$_2$, wherein R has the foregoing definition, and a polymeric formaldehyde in the presence of sulfuric acid catalyst and an inert organic liquid diluent while removing the water formed in the reaction by distillation with said liquid diluent, wherein the improvement comprises effecting the reaction in the presence of at least 0.05 mol sulfuric acid per mol of said amide.

2. The process of claim 1, wherein the amount of sulfuric acid ranges about from 0.1 to 0.5 mol per mol of said amide.

3. The process of claim 1, wherein the amount of polymeric formaldehyde is equivalent to about from 2 to 10 mols of formaldehyde per mol of said amide.

4. The process of claim 1, wherein the amide is propionamide.

5. The process of claim 1, wherein the amide is acetamide.

6. The process of claim 1, wherein the polymeric formaldehyde is paraformaldehyde.

7. The process of claim 1, wherein the organic liquid is selected from the group consisting of toluene, 1,2-dichloroethane and chloroform.

8. The process of claim 1, wherein the reaction is carried out at a temperature in the range of about from 60°C. to 120°C.

* * * * *